United States Patent [19]

Ikeda et al.

[11] Patent Number: 5,541,218

[45] Date of Patent: Jul. 30, 1996

[54] INDOLINYL N-HYDROXYUREA AND N-HYDROXAMIC ACID DERIVATIVES AS LIPOXYGENASE INHIBITORS

[75] Inventors: Takafumi Ikeda; Rodney W. Stevens, both of Handa, Japan

[73] Assignee: Pfizer Inc., New York, N.Y.

[21] Appl. No.: 374,674

[22] PCT Filed: Jun. 10, 1993

[86] PCT No.: PCT/US93/05391

§ 371 Date: Mar. 24, 1995

§ 102(e) Date: Mar. 24, 1995

[87] PCT Pub. No.: WO94/02459

PCT Pub. Date: Feb. 3, 1994

[30] Foreign Application Priority Data

Jul. 23, 1992 [JP] Japan ........................ 4-197242

[51] Int. Cl.⁶ .................. C07D 209/08; A61K 31/40
[52] U.S. Cl. ................................ 514/419; 548/491
[58] Field of Search ........................ 548/491; 514/419

[56] References Cited

U.S. PATENT DOCUMENTS 5,132,319  7/1992  Girand et al. ...................... 514/415

5,187,192  2/1993  Brooks et al. ..................... 514/495

FOREIGN PATENT DOCUMENTS 0279263  8/1988  European Pat. Off. .
0416609  2/1993  European Pat. Off. .
9111298  7/1992  WIPO .

Primary Examiner—Mukund J. Shah
Assistant Examiner—Matthew V. Grumbling
Attorney, Agent, or Firm—Peter C. Richardson; Paul H. Ginsburg; Seymour G. Bekelnitzky

[57] ABSTRACT

Certain indoline derivatives of the formula I:

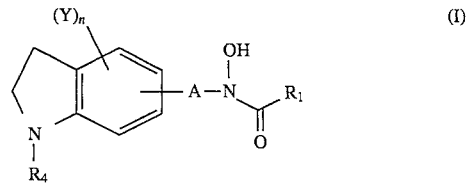

wherein the variables Y, A, $R_1$, $R_4$ and n have the definitions set forth in the disclosure, have the ability to inhibit the 5-lipoxygenase enzyme. These compounds are useful in the treatment or alleviation of inflammatory diseases, allergic conditions and cardiovascular diseases in mammals and as the active ingredient in pharmaceutical compositions for treating such conditions.

8 Claims, No Drawings

INDOLINYL N-HYDROXYUREA AND N-HYDROXAMIC ACID DERIVATIVES AS LIPOXYGENASE INHIBITORS

This invention relates to novel N-hydroxyurea and hydroxamic acid compounds. The compounds of the present invention inhibit the action of lipoxygenase enzyme and are useful in the treatment or alleviation of inflammatory diseases, allergy and cardiovascular diseases in mammals, especially human subjects. This invention also relates to pharmaceutical compositions comprising such compounds.

BACKGROUND OF THE INVENTION

Arachidonic acid is known to be the biological precursor of several groups of endogenous metabolites, prostaglandins including prostacyclins, thromboxanes and leukotrienes. The first step of the arachidonic acid metabolism is the release of arachidonic acid and related unsaturated fatty acids from membrane phospholipids, via the action of phospholipase A2. Free fatty acids are then metabolized either by cyclooxygenase to produce the prostaglandins and thromboxanes or by lipoxygenase to generate hydroperoxy fatty acids which maybe further converted to the leukotrienes. Leukotrienes have been implicated in the pathophysiology of inflammatory diseases, including rheumatoid arthritis, gout, asthma, ischemia reperfusion injury, psoriasis and inflammatory bowel diseases. Any drug that inhibits lipoxygenase is expected to provide significant new therapy for both acute and chronic inflammatory conditions.

Recently several review articles on lipoxygenase inhibitors have been reported. See H. Masamune and L. S. Melvin, Sr.: Annual Reports in Medicinal Chemistry, 24 (1989) pp 71–80 (Academic), and B. J. Fitzsimmons and J. Rokach: Leukotrienes and Lipoxygenases (1989) pp 427–502 (Elsevier).

Compounds of similar structure to the object compounds of the present invention are disclosed in EP 279263 A2, WO 89/04299 and WO 91/16298.

The present inventors have worked to prepare compounds capable of inhibiting the action of lipoxygenase and after extensive research they have succeeded in synthesizing a series of compounds as disclosed in detail herein.

SUMMARY OF THE INVENTION

The present invention provides novel N-hydroxyurea and hydroxamic acid derivatives of the following chemical formula (I) and pharmaceutically acceptable salts thereof;

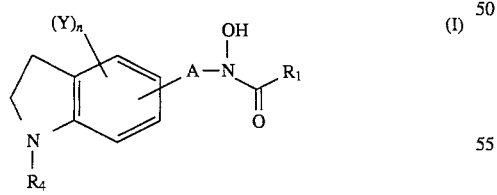

wherein $R_1$ is $C_1$–$C_4$ alkyl or —$NR_2R_3$;

$R_2$ and $R_3$ are each, independently, hydrogen or $C_1$–$C_4$ alkyl; $R_4$ is $C_3$–$C_6$ cycloalkyl, $C_4$–$C_7$ cycloalkylalkyl, aryloxy $C_2$–$C_4$ alkyl, arylthio $C_2C_4$ alkyl, arylamino $C_2$–$C_4$ alkyl, arylsulfinyl $C_2$–$C_4$ alkyl, aryl, aryl $C_1$–$C_6$ alkyl, aryloxyaryl $C_1$–$C_6$ alkyl or arylthioaryl $C_1$–$C_6$ alkyl, and the aryl groups in the said aryloxyalkyl, arylthioalkyl, arylaminoalkyl, arylsulfinylalkyl, aryl, arylalkyl, aryloxyarylalkyl and arylthioarylalkyl may be substituted up to the maximal number of substituents and the substituents are each, independently, selected from the group consisting of halo, cyano, $C_1$–$C_5$ alkyl, $C_2$–$C_6$ alkenyl, $C_1$–$C_5$ alkoxy, $C_2$–$C_6$ alkenyloxy, $C_2$–$C_6$ alkoxyalkyl, halosubstituted $C_1$–$C_4$ alkyl, halosubstituted $C_1C_4$ alkoxy, $C_2$–$C_5$ alkoxycarbonyl, aminocarbonyl and $C_1$–$C_4$ alkylthio;

A is $C_1$–$C_6$ alkylene, $C_3$–$C_6$ alkenylene or —O—$(CH_2)_m$—;

Y is each, independently, halogen, halosubstituted $C_1$–$C_6$ alkyl, $C_1$–$C_6$ alkyl, $C_2$–$C_6$ alkenyl, $C_1$–$C_6$ alkoxy or $C_3$–$C_8$ alkenyloxy;

m is 2, 3 or 4;

n is 0, 1, 2 or 3;

and provided that the substituent Y, if present, and the linking group A are attached to the aromatic ring.

DETAILED DESCRIPTION OF THE INVENTION

In this application, the term "halo" is used herein to mean fluoro, chloro, bromo or iodo.

the term "alkyl" is used herein to mean straight or branched hydrocarbon chain radicals including, but not limited to, methyl, ethyl, n-propyl, isopropyl, n-butyl, and the like;

the term "alkoxy" is used herein to mean —$OR_5$ ($R_5$ is alkyl) including, but not limited to, methoxy, ethoxy, propoxy, isopropoxy, n-butoxy and the like;

the term "alkylthio" is used herein to mean —$SR_6$ ($R_6$ is alkyl) including, but not limited to, methylthio, ethylthio, n-propylthio, isopropylthio, n-butylthio and the like;

the term "alkenyl" is used herein to mean straight or branched hydrocarbon chain radicals having one double bond including, but not limited to, ethenyl, 1- and 2-propenyl, 2-methyl-1-propenyl, 1- and 2-butenyl and the like;

the term "alkenyloxy" is used herein to mean —$OR_7$ ($R_7$ is alkenyl) including, but not limited to, ethenyloxy, 1- and 2-propenyloxy, 2-methyl-1-propenyloxy, 1- and 2-butenyloxy and the like;

the term "alkylene" is used herein to mean optionally straight and branched hydrocarbon chain spacer radicals including, such as —$CH_2$—, —$CH(CH_3)$—, —$CH_2CH_2$—, —$CH_2CH(CH_3)$—and the like;

the term "alkenylene" is used herein to mean straight or branched hydrocarbon chain spacer radicals having one double bond including, such as —CH=CH—, —CH=$CHCH_2$—, —CH=CHCH($CH_3$)—and the like;

the term "alkoxyalkyl" is used herein to mean —$R_8OR_9$ ($R_8$ is alkylene and $R_9$ is alkyl) including, but not limited to, methoxymethyl, ethoxymethyl, n-propoxymethyl, isopropoxymethyl, n-butoxymethyl, isobutoxymethyl, t-butoxymethyl and the like;

the term "cycloalkyl" is used herein to mean cyclic hydrocarbon radicals including, but not limited to, cyclopropyl, cyclobutyl, cyclopentyl, cyclohexyl and the like;

the term "cycloalkylalkyl" is used herein to mean an alkyl radical which is substituted by cycloalkyl group including, but not limited to, cyclopropylmethyl, cyclobutylmethyl, cyclopentylethyl, cyclohexylmethyl and the like;

the term "halosubstituted alkyl" refers to an alkyl radical as described above substituted with one or more halogens including, but not limited to, chloromethyl, bromoethyl, trifluoromethyl and the like;

the term "halosubstituted alkoxy" is used herein to mean refers to an alkoxy radical as described above substituted with one or more halogens including, but not limited to, chloromethoxy, bromoethoxy, difluoromethoxy, trifluoromethoxy and the like;

the term "alkoxycarbonyl" is used herein to mean —COOR$_{10}$ (R$_{10}$ is alkyl) including, but not limited to, methoxycarbonyl, ethoxycarbonyl, propoxycarbonyl and the like;

the term "aryl" is used herein to mean aromatic radicals including, but not limited to, phenyl, naphthyl, pyridyl, quinolyl, thienyl, furyl, benzothienyl, benzofuryl and the like;

the term "arylene" is used herein to mean bivalent aromatic radicals including, but not limited to, o-phenylene, m-phenylene and the like;

the term "arylalkyl" is used herein to mean an alkyl radical which is substituted by aryl group including, but not limited to, benzyl, phenethyl, phenylpropyl, pyridylmethyl, thienylmethyl, furylmethyl and the like;

the term "aryloxy" is used herein to mean —O—Ar$_1$ (Ar$_1$ is aryl) including, but not limited to, phenoxy, naphthoxy, pyridyloxy and the like;

the term "arylthioalkyl" is used herein to mean —R$_{11}$—S—Ar$_2$ (R$_{11}$ is alkylene and Ar$_2$ is aryl) including, but not limited to, phenylthioethyl and the like;

the term "aryloxyalkyl" is used herein to mean —R$_{12}$—O—Ar$_3$ (R$_{12}$ is alkylene and Ar$_3$ is aryl) including, but not limited to, phenyloxyethyl, pyridyloxypropyl and the like;

the term "arylsulfinylalkyl" is used herein to mean —R$_{13}$—SO—Ar$_4$ (R$_{13}$ is alkylene and Ar$_4$ is aryl) including, but not limited to, phenylsulfinylethyl, pyridylsulfinylpropyl and the like;

the term "arylaminoalkyl" is used herein to mean —R$_{14}$—N(R$_{15}$)—Ar$_5$ (R$_{14}$ is alkylene, R$_{15}$ is hydrogen or alkyl and Ar$_5$ is aryl) including, but not limited to, phenylaminoethyl, N-phenyl-N-methylaminoethyl and the like;

the term "aryloxyarylalkyl" is used herein to mean —R$_{16}$—Ar$_6$—O—Ar$_7$ (R$_{16}$ is alkyl, Ar$_6$ is arylene and Ar$_7$ are aryl) including, but not limited to, phenoxybenzyl, pyridyloxyphenethyl and the like; and the term "arylthioarylalkyl" is used herein to mean —R$_{17}$—Ar$_8$—S—Ar$_9$ (R$_{17}$ is alkyl, Ar$_8$ is arylene and Ar$_9$ are aryl) including, but not limited to, phenylthiobenzyl, pyridylthiophenethyl and the like.

General Synthesis

The compounds of formula (I) may be prepared by a number of synthetic methods.

In one embodiment, compounds of the formula (IV) are prepared according to the reaction steps outlined in Scheme 1.

Scheme 1

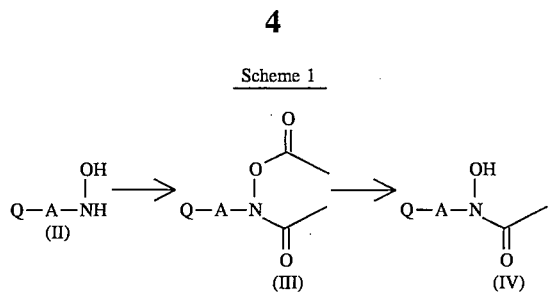

where Q is:

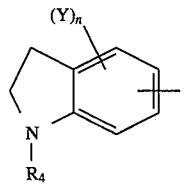

In the first step the diacetyl compound (III) is prepared by standard methods known in the art. For example, the hydroxylamine (II) is reacted with acetyl chloride or acetic anhydride in a reaction-inert solvent in the presence of a suitable base. Preferred basic agents are triethylamine and pyridine, however sodium hydride can be utilized. Suitable reaction-inert solvents include methylene chloride, chloroform, tetrahydrofuran, benzene and toluene. The reaction is usually carried out in the temperature range of 0° C. through to ambient temperature. Reaction times of from 30 minutes to a few hours are common. The product can be isolated and purified by conventional procedures, such as re, crystallization or chromatography.

The second step involves selective hydrolysis of (III) with an appropriate base. The basic agents suitably employed in this reaction include ammonia hydroxide, sodium hydroxide, potassium hydroxide and lithium hydroxide preferably in methanol, ethanol, isopropyl alcohol or water, though binary solvent systems such as alcohol-water, tetrahydrofuran-water and the like may be employed. Reaction temperature is usually in the temperature range of −10° C. through to ambient temperature and the reaction is usually complete within a few minutes to several hours. The product of formula (IV) is isolated by standard methods and purification can be achieved by conventional means, such as recrystallization and chromatography.

In another embodiment, compounds of the formula (V) are prepared as illustrated in Scheme 2.

Scheme 2

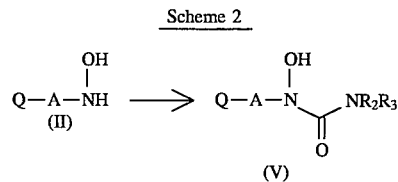

For example, the hydroxylamine (II) is treated with trimethylsilyl isocyanate in a reaction-inert solvent usually at ambient through to reflux temperature to give the compound (V) in which R$_2$ and R$_3$ are both hydrogen. Suitable solvents which do not react with reactants and/or products are, for example, tetrahydrofuran, dioxane, methylene chloride or benzene. Similarly, N-hydroxy-N'-alkylurea compounds (R$_2$ is hydrogen, R$_3$ is alkyl) can be prepared by treating the hydroxylamine (II) with a suitable alkyl isocyanate in place of trimethylsilyl isocyanate. An alternative procedure employs treatment of (II) with gaseous hydrogen chloride in a reaction-inert solvent such as benzene or toluene and then subsequent treatment with phosgene. Reaction temperatures are usually in the range of ambient temperature through to boiling point of solvent. The intermediate carbamoyl chloride is not isolated but subjected to (i.e. in situ) reaction with aqueous ammonia, a primary amine ($R_3NH_2$) or a secondary amine ($R_2R_3NH$). This gives compounds of formula (V), wherein $R_2$ and $R_3$ are each hydrogen, $R_2$ is hydrogen and $R_3$ is alkyl, $R_2$ and $R_3$ are both alkyl, respectively. The product of formula (V) thus obtained is isolated by standard methods and purification can be achieved by conventional means, such as recrystallization and chromatography.

The aforementioned hydroxylamine (II) is easily prepared by standard synthetic procedures from readily available carbonyl compound, i.e. ketone or aldehyde, or alcohol or halogen compound. For example, suitable carbonyl compound is converted to its oxime and then reduced to the requisite hydroxylamine (II) with a suitable reducing agent (for example, see R. F. Borch et at, J. Am. Chem. Soc., 93, 2897, (1971). Reducing agents of choice are, but not limited to, sodium cyanoborohydride and borane complexes such as borane-pyridine, borane-triethylamine and boranedimethylsulfide, however triethylsilane in trifluoroacetic acid may also be employed.

Alternatively the hydroxylamine (II) can be prepared by treating the corresponding alcohol with N,O-bis(tert-butyloxycarbonyl)hydroxylamine under Mitsunobu-type reaction conditions followed by acid catalyzed hydrolysis of the N,O-protected intermediate product. N,O-Diacetyl compound (III) can be prepared employing N,O-diacetyl hydroxylamine in place of N,O-bis(tert-butyloxycarbonyl)hydroxylamine thus providing a convenient route to product of formula (III).

The aforementioned hydroxylamine (II) may also be prepared from suitable halide compound by the reaction with O-protected hydroxylamine and subsequent deprotection (see W. P. Jackson et. al., J. Med. Chem., 31,499, 1988). Preferred O-protected hydroxylamines are, but not limited to, O-tetrahydropyranyl-, O-trimethylsilyl- and O-benzylhydroxylamine.

The requisite synthetic intermediate, carbonyl compound (ketone or aldehyde) is easily prepared by standard synthetic procedures from a readily available indoline compound. For example, a suitable indoline compound is treated with Vilsmeier reagent or with suitable acid chloride or anhydride under Friedel Crafts reaction condition to give a formy- or alkylcarbonylindoline analog respectively. For typical reaction condition, see Jerry March, Advanced Organic Chemistry, Third Ed., pp 484–488 (1985).

Requisite synthetic intermediate, alcohol compounds are easily prepared by standard synthetic procedures from readily available carbonyl compound (eg. aldehyde, ketone or ester) by reduction with conventional reducing agents such as $NaBH_4$, $LiAlH_4$, $BH_3$.THF complex and the like.

Some compounds having asymmetric center of the present invention are capable of occurring in various stereoisomeric forms or configurations. Hence, the compounds can exist in separated (+)- and (−)-optically active forms, as well as in racemic or (±)-mixtures thereof, and in the case of those compounds with two or more asymmetric centers, they can additionally exist as diastereomers with respective optical isomers thereof. The present invention is meant to include all such forms within its scope. For instance, the diastereomers can be separated by fractional crystallization and the like, while the optically-active isomers can be obtained by simply resolving the chemistry that are known for these purposes.

The pharmaceutically acceptable salts of the novel compounds of the invention are readily prepared by contacting said compounds with a stoichiometric amount of an appropriate metal hydroxide or alkoxide or amine in either aqueous solution or a suitable organic solvent. The respective salts may then be obtained by precipitation or by evaporation of the solvent.

The compounds of this invention inhibit the activity of lipoxygenase enzyme. This inhibition has been demonstrated by an assay using rat peritoneal cavity resident cells which determines the effect of said compounds on the metabolism of arachidonic acid.

All of the following examples 1 to 18 were tested according to the methods described in Jap. J. Inflammation 7: 145–150 (1987), "Synthesis of leukotrienes by peritoneal macropharges" and those were shown to possess the efficacy of inhibiting lipoxygenase activity.

In this test some preferred compounds indicated low $IC_{50}$ values, in the range of 0.01 to 30μM, with respect to lipoxygenase activity.

The ability of the compounds of the present invention to inhibit lipoxygenase enzyme makes them useful for controlling the symptoms induced by the endogenous metabolites arising from arachidonic acid in a mammalian subject, especially a human subject. The compounds are therefore valuable in the prevention and treatment of such disease states in which the accumulation of arachidonic acid metabolites are the causative factor; e.g. allergic bronchial asthma, skin disorders, rheumatoid arthritis, osteoarthritis and thrombosis.

Thus, the compounds of the present invention and their pharmaceutically acceptable salts are of particular use in the treatment or alleviation of inflammatory diseases in a human subject.

For treatment of the various conditions described above, the compounds and their pharmaceutically acceptable salts can be administered to a human subject either alone, or preferably in combination with pharmaceutically acceptable careers or diluents in a pharmaceutical composition according to standard pharmaceutical practice.

The compounds can be administered by various conventional routes of oral and parenteral administration and by inhalation. When the compounds are administered orally, the dose range will be from about 0.1 to 20 mg/kg per body weight of the subject to be treated per day, preferably from about 0.1 to 1.0 mg/kg per day in single or divided doses. If parenteral administration is desired, then an effective dose will be from about 0.1 to 1.0 mg/kg per body weight of the subject to be treated per day. In some instances it may be necessary to use dosages outside these limits, since the dosages will necessarily vary according to the age, weight and response of the individual patient as well as the severity of the patient's symptoms and the potency of the particular compound being administered.

For oral administration, the compounds of the invention and their pharmaceutically acceptable salts can be administered, for example, in the form of tablets, powders, lozenges, syrups or capsules or as an aqueous solution or suspension. In the case of tablets for oral use, carriers which are commonly used include lactose and corn starch. Further lubricating agents such as magnesium stearate are commonly added. In the case of capsules, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared and the pH of the solutions should be suitably adjusted and buffered. For intravenous use, the total concentration of solute should be controlled to make the preparation isotonic.

The present invention is illustrated by the following examples. However, it should be understood that the invention is not limited to the specific details of these examples. Proton nuclear magnetic resonance spectra (NMR) were measured at 270 MHz unless otherwise indicated and peak positions are expressed in parts per million (ppm) downfield from tetramethylsilane. The peak shapes are denoted as follows: s-singlet, d-doublet, t-triplet, q-quartet, quint-quintet, m-multiplet, br-broad.

EXAMPLE 1

N-(1-Benzylindolin-5-yl)methyl-N-hydroxyurea

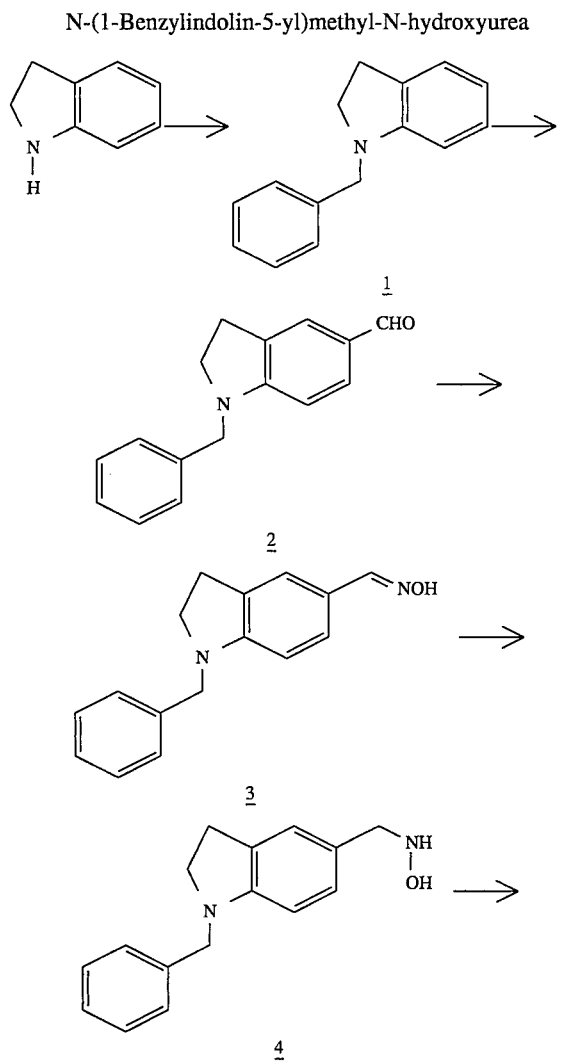

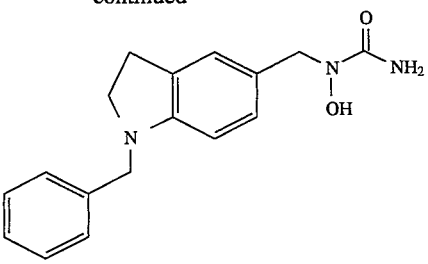

5

(A) 1-Benzyl-5-formylindoline, 2

To a solution of indoline (2.8 ml, 25.2 mmol) in THF (60 ml) was added 1.65N-n-BuLi (16 ml, 26.5 mmol) at −68° C. under a nitrogen atmosphere and the mixture was stirred for 35min. To the mixture was added benzylbromide (3.2 ml, 26.5 mmol) at −68° C. and the whole stirred at −68° C. for 15min and then allowed to stand at ambient temperature for 2 hr. $H_2O$ (20 ml) was added and the mixture extracted with ethyl acetate (50 ml×2). The extracts were combined, washed with brine (50 ml×2), dried over $MgSO_4$ and evaporated in vacuo to give a light brown oil (1, 5.16 g).

A solution of the product in DMF (13 ml) was added to a mixture of $POCl_3$ (3.52 ml, 37.8 mmol) in DMF (38 ml) at room temperature and stirred for 2 hr under a nitrogen atmosphere. $H_2O$ (20 ml) was added and the whole concentrated in vacuo. The resulting residue was extracted with ethyl acetate (50 ml×3) and the extracts were combined, washed with saturated $NaHCO_3$ solution (50 ml) and brine (50 ml), dried over $MgSO_4$ and evaporated in vacuo. Chromatography on silica gel (80 g) eluted with hexane/ethyl acetate (4:1) to give a light yellow oil (2, 2.82 g, 47.2% yield). NMR ($CDCl_3$) δ: 9.68 (s, 1H), 7.53–7.60 (m, 2H), 7.27–7.41 (m, 5H), 6.47 (d, J=8.1 Hz, 1H), 4.42 (s, 2H), 3.58 (t, J=8.6 Hz, 2H), 3.08 (t, J=8.8 Hz, 2H).

(B) N-(1-Benzylindolin-5-yl)methyl-N-hydroxyurea, 5

To a solution of the aldehyde (2, 2.75 g, 11.6 mmol) in EtOH (11.6 ml) and pyridine (11.6 ml) was added hydroxylamine hydrochloride (1.25 g, 17.4 mmol) at ambient temperature. The mixture was stirred at ambient temperature for 1.7 hr. The whole was concentrated in vacuo and the resulted residue was partitioned between ethyl acetate (50 ml) and $H_2O$ (20 ml). The aqueous layer was extracted with ethyl acetate (50 ml). The organic extracts were combined, washed with brine (50 ml×2) and dried over $MgSO_4$ to give light yellow solid (3, 3.71 g).

The oxime (3, 3.71 g) was dissolved in acetic acid (23.2 ml, 0.403 mol) and $NaB(CN)H_3$ (889mg, 13.4 mmol) was added portionwise to the solution during a period of 2 hr. The mixture was stirred for further 30 min, then cooled in an ice bath and neutrized with 10N-NaOH (38.2 ml, 0.382 mol) and then 10% aqueous $K_2CO_3$. The mixture was extracted with ethyl acetate (50 ml×2) and washed with saturated NaCl solution (50 ml×2). The organic layer was dried over $MgSO_4$ and evaporated to give a yellow oil (4, 3.07 g).

To a solution of the hydroxylamine (4, 3.07 g) in dry THF (23mi) was added trimethylsilyl isocyanate (2.77 ml, 17.4 mmol) and the whole was stirred overnight under nitrogen atmosphere. The mixture was concentrated in vacuo to give a yellow oil (4.51 g). Chromatography on silica gel (100 g) eluted with $CH_2Cl_2$/ethyl acetate/MeOH (30:1:1) to give white solids. Recrystallization from ethyl acetate gave N-(1-benzylindolin-5-yl)methyl-N-hydroxyurea (5, 2.26 g, 65.5%) as white solids. m.p.: 106.8°–107.2° C.

IR (KBr) cm$^{-1}$: 3476, 3171, 2801, 1639, 1598, 1494, 1444, 1148, 1081, 695.

NMR (DMSO-d$_6$) δ: 9.18 (d, J=2.2 Hz, 1H), 7.31–7.38(m, 4H), 7.22–7.30(m, 1H), 6.98 (s, 1H), 6.90 (d, J=7.7 Hz, 1H), 6.50 (d, J=8.1 Hz, 1H), 6.22 (s, 2H), 4.35 (s, 2H), 4.24 (s, 2H), 3.23 (t, J=8.4 Hz, 2H), 2.86 (t, J=8.2 Hz, 2H).

EXAMPLE 2

N-Hydroxy-N-{1-(3-phenylpropyl)indolin-5-yl}-methylurea

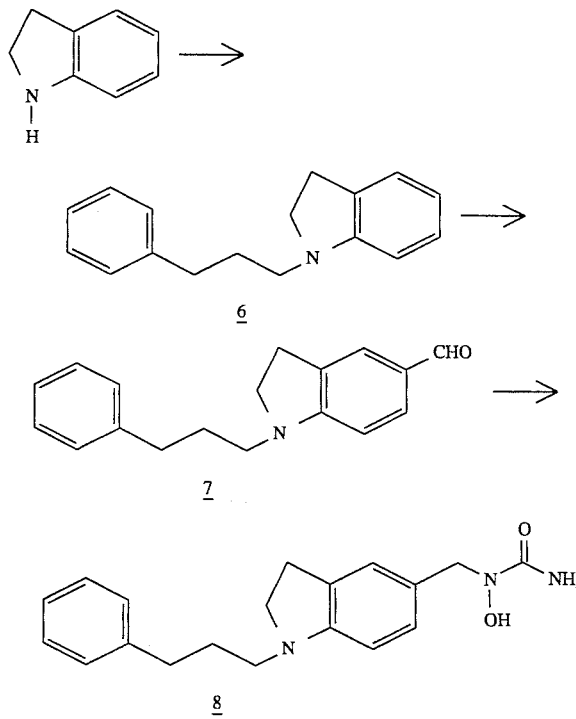

(A) 1-(3-Phenylpropyl)indoline 6

To a solution of indoline (2.5 ml, 20 mmol) in dry toluene (5 ml) was added hydrocinnamoyl chloride (3.1 ml, 21 mmol) to give white solids. The mixture was stirred at reflux under a nitrogen atmosphere for 1 hr. The mixture was concentrated in vacuo to give ivory color solids. This was suspended in dry tetrahydrofuran (28 ml). To the suspension was added BH$_3$.SMe$_2$ (3.8 ml, 40 mmol) and stirred at room temperature for 30 min and then at reflux for 2 hr under a nitrogen atmosphere. To the mixture was carefully added Na$_2$SO$_4$.10H$_2$O (excess), then H$_2$O added. The whole was extracted with ethyl acetate (50 ml), washed with brine (10 ml), dried over MgSO$_4$ and concentrated in vacuo to give yellow oil (5.1 g). Chromatography on silica gel (50 g) eluted with hexane-ethyl acetate (30:1) gave a colorless oil (6, 4.05 g, 85%).

NMR (CDCl$_3$) δ7.15–7.33 (m, 5H), 7.01–7.09 (m, 2H), 6.63(t, J=7.3 Hz, 1H), 6.41 (d, J=7.7 Hz, 1H), 3.34 (t, J=8.4 Hz, 2H), 3.07 (t, J=7.2 Hz, 2H), 2.96 (t, J=8.2 Hz, 2H), 2.73 (t, J=7.7 Hz, 2H), 1.93 (quint, J=7.4 Hz, 2H).

(B) 1-(3-Phenylpropyl)-5-formylindoline, 7

POCl$_3$ (2.39 ml) was added to DMF (25 ml) and the mixture was stirred at room temperature under a nitrogen atmosphere for 1 hr. To the mixture was added compound (6, 4.05 g, 17.1 mmol) in DMF (9 ml) and stirred at room temperature for 2 hr. H$_2$O (5 ml) was added and concentrated in vacuo to give a dark green oil. The resulted residue was partitioned between ethyl acetate (150 ml) and H$_2$O (70 ml). The aqueous layer was extracted with ethyl acetate (50 ml). The extracts were combined, washed with brine (30 ml), saturated NaHCO$_3$ solution (30 ml) and brine (30 ml). The solution was dried over MgSO$_4$ and concentrated in vacuo to give a dark green oil. Chromatography on silica gel (50 g) eluted with hexane-ethyl acetate (5:1) gave a yellow oil (7, 3.09 g, 68.2%).

NMR (CDCl$_3$) δ9.65 (s, 1H), 7.50–7.57 (m, 2H), 7.16–7.34 (m, 5H), 6.28 (d, J=8.8 Hz, 1H), 3.59 (t, J=8.4 Hz, 2H), 3.22 (t, J=7.3 Hz, 2H), 3.04 (t, J=8.6 Hz, 2H), 2.70 (t, J=7.5 Hz, 2H), 1.95 (quint, J=7.5 Hz, 2H).

(C) N-Hydroxy-N-{1-(3-phenylpropyl)indolin-5-yl}methylurea, 8

N-Hydroxy-N-{1-(3-phenylpropyl)indolin-5-yl }methylurea, 8 was prepared from compound 7 according to the procedure of Example 1, Part (B).

m.p.: 94.0°–94.5° C.

IR (KBr) cm$^{-1}$: 3470, 3330, 3190, 2950, 2800, 1618, 1575, 1497.

NMR (DMSO-d$_6$) δ: 9.16 (s, 1H), 7.14–7.32 (m, 5H), 6.96 (s, 1H), 6.89 (d, J=8.1 Hz, 1H), 6.33 (d, J=8.1 Hz, 1H), 6.22 (s, 2H), 4.34 (s, 2H), 3.27 (t, J=8.3 Hz, 2H), 3.01 (t, J=7.2Hz, 2H), 2.85 (t, J=8.3 Hz, 2H), 2.66 (t, J=7.7 Hz, 2H), 1.83 (quint, J=7.3 Hz, 2H).

EXAMPLE 3

N-Hydroxy-N-(1-phenylindolin-5-yl)methylurea

A synthetic intermediate, N-phenylindoline was prepared by known reaction procedures. See the following references; Gordon N. Walker, Ronald T. Smith, and Barbara N. Weaver, J. Med. Chem., 8, p. 626, 1965, Heinz Sirowej, Shafiq Ahmad Khan and Hans Plieninger, Synthesis, p. 84, 1972, Bruce E. Martanoff and David F. McComsey, J. Org. Chem., 43, p. 2733, 1978.

Conversion to the title compound was achieved by following the procedure of Example 1.

m.p.: 143.0°–143.3° C.

IR (KBr) cm$^{-1}$: 3490, 3320, 2860, 1625, 1580, 1510, 1380, 1325. NMR (DMSO-d$_6$) δ: 9.23 (s, 1H), 7.34 (t, J=7.8 Hz, 2H), 7.21 (d, J=7.7 Hz, 2H), 7.11 (s, 1H), 7.03 (d, J=8.1 Hz, 1H), 6.89–6.99 (m, 2H), 6.26 (s, 2H), 4.40 (s, 2H), 3.91 (t, J=8.4 Hz, 2H), 3.06 (t, J=8.4 Hz, 2H).

The compounds of Examples 4, 5, 6, 7, 8, 9, 10 and 11 were prepared in the same manner used for the preparation of compounds of EXAMPLE 1.

EXAMPLE 4

N-Hydroxy-N-{1-(3-methoxybenzyl)indolin-5-yl}methylurea m.p.: 73.4°–74.5° C.

IR (KBr) cm$^{-1}$: 3516, 3234, 2806, 1660, 1629, 1581, 1489, 1265, 1141, 1044, 789, 765, 697, 506.

NMR (DMSO-d$_6$) δ: 9.05 (s, 1H), 7.13 (t, J=7.9Hz, 1H), 6.86 (s, 1H), 6.74–6.83 (m, 3H), 6.71 (dd, J=8.6, 1.8 Hz, 1H), 6.37 (d, J=8.1 Hz, 1H), 6.10 (s, 2H), 4.23 (s, 2H), 4.08 (s, 2H), 3.61 (s, 3H), 3.12 (t, J=8.2 Hz, 2H), 2.74 (t, J=8.2 Hz, 2H).

EXAMPLE 5

N-Hydroxy-N-{1-(3-trifluoromethylbenzyl)indolin-5-yl}methylurea m.p.: 109.3°–109.9° C.

IR (KBr)cm$^{-1}$: 3500, 3242, 2847, 1640, 1575, 1500, 1454, 1352, 1327, 1265, 1108, 951, 797, 700.

NMR (DMSO-d$_6$) δ9.19 (s, 1H), 7.55–7.79 (m, 4H), 7.01 (s, 1H), 6.91 (d, J=7.7 Hz, 1H), 6.50 (d, J=8.1 Hz, 1H), 6.24 (s, 2H), 4.37 (s, 2H), 4.34 (s, 2H) 3.26 (t, J=7.9 Hz, 2H), 2.89 (t, J=7.9 Hz, 2H).

EXAMPLE 6

N-{1-(3-Cyanobenzyl)indolin-5-yl}methyl-N-hydroxyurea m.p.: 97.1°–98.0 C.

IR (KBr) cm$^{-1}$: 3500, 3345, 2829, 2224, 1644, 1574, 1492, 1249, 818, 780, 683.

NMR (DMSO) δ9.19 (s, 1H), 7.79 (s, 1H), 7.74 (d, J=7.7 Hz, 1H), 7.69 (d, J=8.1 Hz, 1H), 7.56 (t, J=7.7 Hz, 1H), 6.99 (s, 1H), 6.90 (d, J=8.1 Hz, 1H), 6.48 (d, J=8.1 Hz, 1H), 6.22 (s, 2H), 4.36 (s, 2H), 4.30 (s, 2H), 3.26 (t, J=8.4 Hz, 2H), 2.88 (t=8.2 Hz, 2H).

EXAMPLE 7

N-{1-(3-Fluorobenzyl)indolin-5-yl}methyl-N-hydroxyurea m.p.: 106.2°–107.3° C.

IR (KBr)cm$^{-1}$: 3435, 3202, 2855, 1673, 1586, 1507, 1450, 1341, 1262, 1119, 949, 773, 681, 500.

NMR (DMSO-d$_6$) δ: 9.18 (s, 1H), 7.34–7.43 (m, 1H), 7.03–7.23 (m, 3H), 7.00 (s, 1H), 6.91 (d, J=8.1 Hz, 1H), 6.48 (d, J=8.1 Hz, 1H), 6.24 (s, 2H), 4.37 (s, 2H), 4.26 (s, 2H), 3.26 (t, J=8.4 Hz, 2H), 2.88 (t, J=8.2 Hz, 2H).

Example 8

N-{1-(3-Chlorobenzyl)indolin-5-yl}methyl-N-hydroxyurea m.p.: 123.6°–123.9° C.

IR (KBr) cm$^{-1}$: 3500, 3186, 2858, 1638, 1571, 1500, 1462, 1352, 1245, 1146, 781, 770, 692.

NMR (DMSO-d$_6$) δ: 9.18 (s, 1H), 7.28–7.42 (m, 4H), 7.00 (s, 1H), 6.90 (d, J=8.1 Hz, 1H), 6.48 (d, J=8.1 Hz, 1H), 6.24 (s, 2H), 4.36 (s, 2H), 4.25 (s, 2H),(s, 2H), 3.26 (t, J=8.2 Hz, 2H), 2.88 (t, J=8.2 Hz, 2H).

EXAMPLE 9

N-Hydroxy-N-{1-(3-methylbenzyl)indolin-5-yl}-methylurea m.p.: 89.4°–89.8° C.

IR (KBr) cm$^{-1}$: 3450, 3350, 3270, 3200, 2860, 1675, 1620, 1587, 1550, 1440, 1410, 1340, 1303, 1278.

NMR (DMSO-d$_6$) δ: 9.16 (s, 1H), 7.22 (t, J=7.4 Hz, 1H),7.12–7.18 (m, 2H), 7.09 (t, J=7.0 Hz, 1H), 6.98 (s, 1H), 6.89 (d, J=7.7 Hz, 1H), 6.48 (d, J=8.0 Hz, 1H),6.23 (s, 2H), 4.35 (s, 2H), 4.18 (s, 2H), 3.22 (t, J=8.3 Hz, 2H), 2.85 (t, J=8.3 Hz, 2H), 2.29 (s, 3H).

EXAMPLE 10

N-{1-(3-Difluoromethoxybenzyl)indolin-5-yl}-methyl-N-hydroxyurea m.p.: 112.0°–112.2° C.

IR (KBr)cm$^{-1}$: 3500, 3230, 2847, 1639, 1570, 1500, 1454, 1351, 1245, 1165, 1120, 1039, 950, 800, 780.

NMR (DMSO-d$_6$) δ: 9.20 (s, 1H), 7.40 (t, J=7.9 Hz, 1H), 7.23 (d, J=7.7 Hz, 1H), 7.23 (t, J=74.2 Hz, 1H), 7.15 (s, 1H), 7.10 (dd, J=1.5, 8.1 Hz, 1), 6.99 (s, 1H), 6.91 (dd, J=1.5, 7.7 Hz, 1H), 6.64 (d, J=8.1 Hz, 1H), 6.24 (s, 2H), 4.36 (s, 2H), 4.26 (s, 2H), 3.26 (t, J=8.2 Hz, 2H), 2.88 (t, J=8.2 Hz, 2H).

EXAMPLE 11

N-(1-Benzylindolin-5-yl)methyl-N'-ethyl-N-hydroxyurea m.p.: 96.5°–97.3° C.

IR (KBr)cm$^{-1}$: 3410, 2850, 1630, 1550, 1480, 1472, 1455, 1360, 1213, 1117.

NMR (DMSO-d$_6$) δ: 9.08 (s, 1H), 7.22–7.38 (m, 5H), 6.96 (s, 1H), 6.89 (d, J=8.1 Hz, 1H),6.81 (t, J=5.7 Hz, 1H), 6.50 (d, J=8.1 Hz, 1H), 4.34 (s, 2H), 4.24 (s, 2H), 3.23 (t, J=8.3 Hz, 2H), 3.01–3.12 (m, 2H), 2.85 (t, J=8.3 Hz, 2H), 1.00 (t, J=7.2 Hz, 3H).

The compounds of Examples 12 and 13 were prepared in the same manner used for the preparation of compounds of Example 2.

EXAMPLE 12

N-Hydroxy-N-{(1-phenoxyethyl)indolin-5-yl}-methylurea m.p.: 122.0°–122.4 C.

IR (KBr)cm$^{-1}$: 3490, 3320, 2890, 2800, 1625, 1580, 1500, 1470, 1377, 1245, 1080, 1053.

NMR (DMSO) δ: 9.17 (s, 1H), 7.23–7.33 (m, 2H), 6.88–7.01 (m, 5H), 6.50 (d J=8.1 Hz, 1H), 6.22 (s, 2H), 4.35 (s, 2H), 4.16 (t, J=5.7 Hz, 2H), 3.38–3.49 (m, 4H), 2.87 (t, J=8.2 Hz, 2H).

EXAMPLE 13

N-Hydroxy-N-[1-{2-(3-methoxyphenyl)ethyl}-indolin-5-yl]methylurea m.p.: –(oil)

IR (CHCl$_3$) cm$^{-1}$: 3550, 3420, 3010, 1675, 1565, 1495, 1440, 1260, 1155.

NMR (DMSO-d$_6$) δ: 9.16 (s, 1H), 7.20 (t, J=8.1 Hz, 1H), 6.96 (s, 1H), 6.77 (br d, J=7.7 Hz, 1H), 6.47 (d, J=8.1 Hz, 1H), 6.22 (s, 2H), 4.34 (s, 2H), 3.74 (m, 4H), 2.74–2.90 (m, 4H).

EXAMPLE 14

N-(1-Benzylindolin-5-yl)methyl-N-hydroxyacetamide

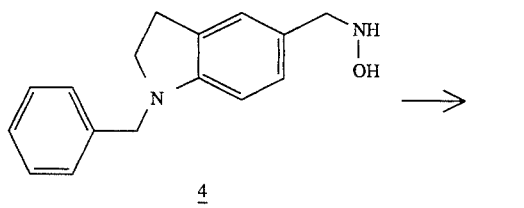

4

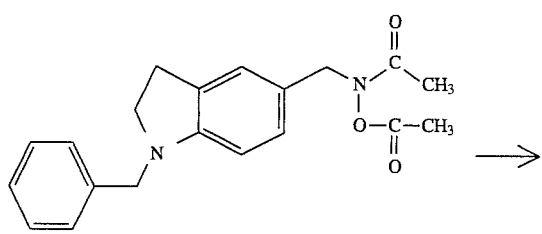

9

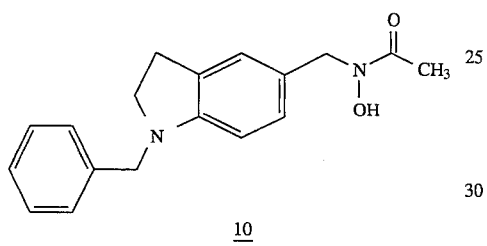

10

(A) N-Acetoxy-N-{(1-benzylindolin-5-yl)methyl}acetamide, 9

To a solution of compound (4, 1.806 g, 7.11 mmol) in pyridine (3 ml) was added acetic anhydride (3 ml). The mixture was stirred at room temperature for 1 hr. The mixture was concentrated in vacuo and the resulted residue was partitioned between ethyl acetate (70 ml) and $H_2O$ (30 ml). The organic layer was washed with saturated $NaHCO_3$ solution (3×20 ml) and brine (20 ml). The solution was dried over $MgSO_4$ and concentrated in vacuo. Chromatography on silica gel (40 g) eluted with hexane-ethyl acetate (2:1) gave a yellow oil (9, 1.29 g, 53.9%).

NMR ($CDCl_3$) δ: 7.21–7.37 (m, 5H), 7.03 (s, 1H), 6.93 (d, J=8.1 Hz, 1H), 6.42 (d, J=8.1 Hz, 1H), 4.74 (s, 2H), 4.24 (s, 2H), 3.34 (t, J=8.3 Hz, 2H), 2.96 (t, J=8.2 Hz, 2H), 2.12 (s, 3H), 2.04 (br s, 3H).

(B) N-(1-Benzylindolin-5-yl)methyl,N-hydroxyacetamide, 10

To a solution of compound (9, 1.29 g, 3.8 mmol) in methanol (4 ml) was added conc. aqueous ammonia (25%, 1.6 ml) and the mixture was stirred at room temperature for 1 hr. The solvents were removed off and the resulted residue was extracted with ethyl acetate (50 ml). The extracts were washed with brine (2×20 ml). The solution was dried over $MgSO_4$ and concentrated in vacuo. Chromatography on silica gel (30 g) eluted with hexane-ethyl acetate (2:1 –1:1) gave N-(1-Benzylindolin-5-yl)methyl-N-hydroxyacetamide, 10 as a colorless oil (0.7 g, 62%).

NMR (DMSO-$d_6$) δ: 9.70 (s, 1H), 7.21–7.39 (m, 5H), 6.96 (s, 1H), 6.89 (d, J=8.1, 1H), 6.51 (d, J=8.1 Hz, 1H), 4.50 (s, 2H), 4.25 (s, 2H), 3.25 (t, J=8.2 Hz, 2H), 2.87 (t, J=8.2 Hz, 2H), 2.87 (t, J=8.2 Hz, 2H), 1.99 (s, 3H).

EXAMPLE 15

N-Hydroxy-N-{1-(3-phenoxybenzyl)indolin-5-yl}-methylurea

The compound of Example 15 was prepared in the same manner used for the preparation of compound of EXAMPLE 1.

m.p.: —(oil)

IR (neat) $cm^{-1}$: 3534, 3032, 1674, 1587, 1565, 1487, 1444, 1248, 1212, 929, 785, 732, 669, 626.

NMR (DMSO) δ: 9.18 (s, 1H), 7.33–7.40 (m, 4H), 7.13 (t, J=7.3 Hz, 1H), 6.94–7.04 (m, 4H), 6.89 (d, J=8.1 Hz, 2H), 6.48 (d, J=8.1 Hz, 1H), 6.22 (s, 2H), 4.35 (s, 2H), 4.23 (s, 2H), 3.16–3.33 (m, 2H), 2.86 (t, J=7.9 Hz, 2H).

EXAMPLE 16

N-Hydroxy-N-{1-(3-methoxybenzyl)indolin-4-yl}-methylurea (A) 4-Hydroxymethyl-1-(3-methoxybenzyl)indole, 13

Methyl indolin-4-carboxylate, 11 was synthesized by known procedures: see Gerald S Ponticello and John J. Baldwin, J. Org. Chem. 44 4003 (1979) and Alan P. Kozikowski, Hitoshi Ishida, and Yon-Yih Chen, 45 3350 (1980).

To a suspension of 60% NaH (2.33 g, 58.4 mmol) in dry THF (167 ml) was added dropwise a solution of methyl indolin-4-carboxylate (9.73 g, 55.6 mmol) in dry

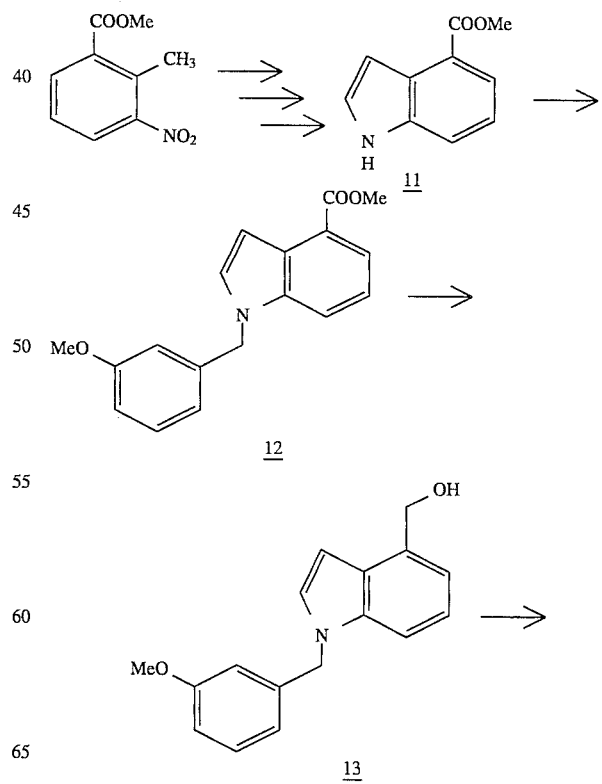

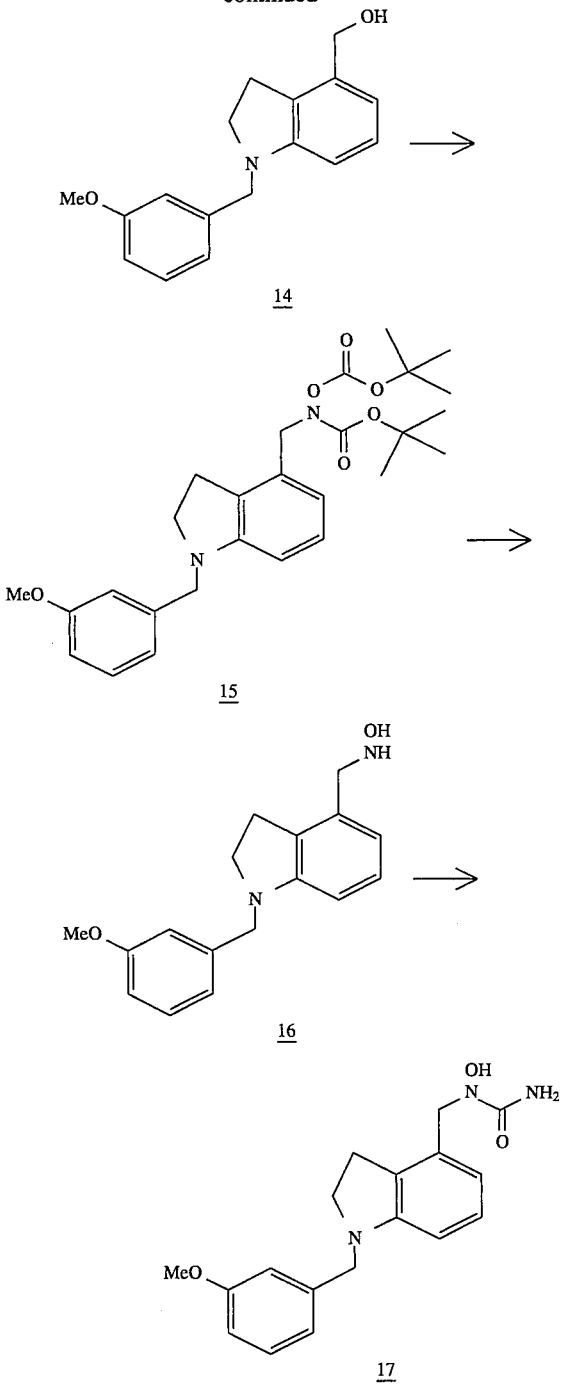

THF (63ml) at 0° C. under nitrogen atmosphere. The mixture was stirred at ambient temperature for 30 min. under nitrogen atmosphere. To the stirred mixture was added 3-methoxybenzylchloride (8.7 ml, 58.3 mmol) and the stirring was continued under nitrogen atmosphere for 2 hr. To the mixture was added H₂O (80 ml) and extracted with ethyl acetate (300 ml and then 100 ml). The combined extracts were washed with saturated aqueous NaCl(80 ml) and dried over MgSO₄ to give 12 as a brown oil (16.51 g, 100%).

NMR (CDCl₃) δ: 7.88–7.94 (m, 1H), 7.24–7.30 (m, 1H), 7.20 (s, 1H), 7.15–7.19 (m, 1H), 6.60–7.00 (m, 5H), 4.56 (s, 2H), 3.99 (s, 3H), 3.72 (s, 3H).

To a cooled solution of the ester 12, 16.51 g, 55.6 mmol) in dry THF (167 ml) at 0° C. was added portionwise LiAlH₄ (3.15 g, 83.3 mmol). The mixture was stirred at 0° C. for 1 hr. under nitrogen atmosphere. To the mixture was added Na₂SO₄·10H₂O and then H₂O to afford white precipitate. The whole was filtered and the resulted cake was washed with ethyl acetate (200 ml). The filtrate and the washings were combined and the organic layer was washed with brine (50 ml). The solution was dried (MgSO₄) and concentrated in vacuo to give a brown oil. Chromatography on silica gel eluted with hexane-ethyl acetate (3:1 to 1:1) gave an alcohol 13 as a brown oil (9.09 g, 61.2 %).

NMR (CDCl₃) δ: 7.10–7.34 (m, 5H), 6.76–6.85 (m, 2H), 6.61–6.74 (m, 2H), 5.30 (s, 2H), 5.00 (s, 2H), 3.73 (s, 3H).

(B) N,O-Dibutoxycarbonyl-N-{1-(3-methoxybenzyl)indolin-4-ylmethyl}hydroxylamine, 15

To a solution of the indole derivative (13, 0.529 g, 1.98 mmol) in acetic acid (5 ml) was added NaBCNH₃ (0.393 g, 5.94 mmol) at 15° C. and stirred at 15° C. for 2 hr. To the mixture was added H₂O (20 ml) and the cooled mixture at 0° C. was neutralized with 1N NaOH solution. The whole was extracted with CH₂Cl₂(50 ml) and the extract was washed with brine (20 ml), dried (MgSO₄) and concentrated in vacuo to give a indoline derivative 14 as a pale yellow oil.

NMR (CDCl₃) δ: 7.20–7.29 (m, 2H), 7.03–7.12 (m, 1H), 6.89–6.97 (m, 2H), 6.78–6.85 (m, 1H), 6.68 (d, J=7.7 Hz, 1H), 6.45 (d, J=7.7 Hz, 1H), 4.59 (s, 2H), 4.22 (s, 2H), 3.78 (s, 3H), 3.35 (t, J=8.4 Hz, 2H), 2.98 (t, J=8.4 Hz, 2H).

To a solution of the alcohol (14, 0.45 g, 1.67 mmol), Ph₃P (0.59 g, 2.17 mmol) and BocNHOBoc (0.411 g, 1.75 mmol) in dry THF (3.5 ml) was added diethyl azodicarboxylate (0.34 ml, 2.2 mmol) at −70° C. under nitrogen atmosphere. The mixture was stirred at ambient temperature under nitrogen atmosphere overnight. The whole was concentrated in vacuo and the resulted triphenyl phosphine oxide was crystallized from hexane-ethyl acetate (3:1) and removed by suction filtration. The filtrate was concentrated in vacuo to give a pale yellow oil (1.579 g). Chromatography on silica gel eluted with hexane-ethyl acetate 5:1 to 2:1) gave 15 as a pale yellow oil (660 mg, 81.5% ).

NMR (CDCl₃) δ: 7.19–7.25 (m, 1H), 7.03 (t, J=7.5 Hz, 1H), 6.88–6.97(m, 2H), 6.78–6.85 (m, 1H), 6.65 (d, J=7.5 Hz, 1H), 6.43 (d, J=7.5 Hz, 1H), 4.68 (br s, 2H), 4.23 (s, 2H), 3.80 (s, 3H), 3.34 (t, J=7.7 Hz, 2H), 3.00 (t, J=7.7 Hz 2H), 1.49 (s, 9H), 1.45 (s, 9H).

(C) N-Hydroxy-N-{1-(3-methoxybenzyl)indoline-4-yl}methylurea, 17

To a solution of compound (15, 0.582 g, 1.2 mmol) in CH₂Cl₂ (12 ml) was added trifluoroacetic acid (2.4 ml) and stirred at ambient temperature under nitrogen atmosphere for 2 hr. To the mixture was added NaHCO₃ solution (10 ml) and extracted with ethyl acetate (50 ml×2). The combined extracts were washed with brine (30 ml), dried (MgSO₄) and concentrated in vacuo to give hydroxylamine 16 as a pale yellow oil (292 mg, 86.2% ).

NMR (CDCl₃) δ: 7.20–7.29 (m, 1H), 7.04 (t, J=7.5 Hz, 1H), 6.87–6.96 (m, 2H), 6.77–6.84 (m, 1H), 6.64 (d, J=7.7 Hz, 1H), 6.44 (d, J=7.7 Hz, 1H), 4.21 (s, 2H), 3.79 (s, 3H), 3.34 (t, J=8.2 Hz, 2H), 3.00 (t, J=8.2 Hz, 2H).

To a solution of the hydroxylamine (16, 292 mg, 1.03 mmol) in dry THF (2.1 ml) was added trimethylisocyanate (0.25 ml, 1.57 mmol). The mixture was stirred at ambient temperature under nitrogen atmosphere for 30 min. The whole was concentrated in vacuo and purified by silica gel chromatography eluted with CH₂Cl₂: MeOH: ethyl acetate= 15:1:1 to 10:1:1) to give white solids. Recrystallization from ethyl acetate-MeOH gave the title compound 17 as a white powder (44.6 mg, 13.2%).

m.p.: 134.4°–135.0 ° C.

IR (KBr) cm$^{-1}$: 3470, 3340, 3251, 1635, 1587, 1448, 1273, 1140, 1052, 769, 752, 693, 608, 524.

NMR (DMSO) δ: 9.25 (s, 1H), 7.25 (t, J=8.1 Hz, 1H), 6.93 (t, J=8.1 Hz, 1H), 6.92 (d, J=8.1 Hz, 1H), 6.89 (s, 1H), 6.80–6.86 (m, 1H), 6.55 (d, J=7.0 Hz, 1H), 6.46 (d, J=7.7 Hz, 1H), 6.27 (s, 2H), 4.41 (s, 2H), 4.22 (s, 2H), 3.24–3.30 (m, 2H), 2.90 (t=8.2 Hz, 2H).

EXAMPLE 17

N-Hydroxy-N-[1-{1-(3-methoxybenzyl)indolin-5-yl}-ethan-1-yl]urea

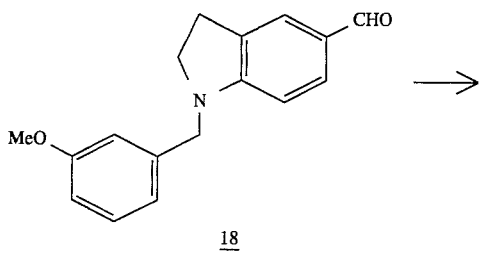

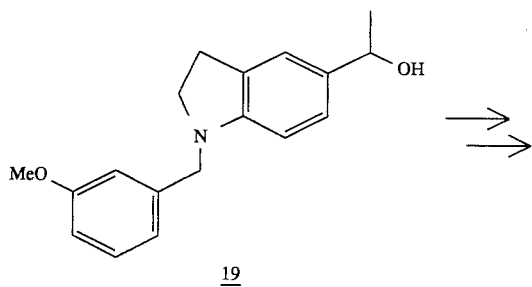

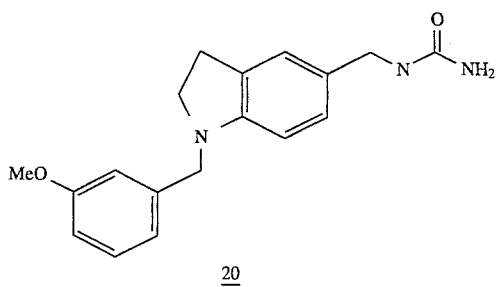

5-(1-Hydroxyethyl)-1-(3-methoxybenzyl)indoline 19

An intermediate of 18 was synthesized in the same manner used for the preparation of compound of Example 1.

To a solution of aldehyde (18, 20.05 g, 75 mmol) in dry THF (200 ml) was added 3.0 M MeMgBr at 0° C. under nitrogen atmosphere. The mixture was stirred at ambient temperature for 30 min. To the mixture was added ice and then hexane (200 ml). The organic layer was washed with brine, dried (MgSO$_4$) and concentrated in vacuo to give a brown oil (18.9 g). Chromatography on silica gel eluted with hexane: ethyl acetate =2:1 to 3:2) gave an light yellow oil (19, 19.61 g, 92.3%).

NMR (CDCl$_3$) δ: 7.21–7.28 (m, 1H), 7.15 (s, 1H), 7.05 (d, J=7.7 Hz, 1H), 6.94 (d, J=7.7 Hz, 1H), 6.93 (s, 1H), 6.79–6.85 (m, 1H), 6.45 (d, J=8.1 Hz, 1H), 4.78–4.82 (m, 1H), 4.21 (s, 2H), 3.80 (s, 3H), 3.33 (t, J=8.4 Hz, 2H), 2.97 (t, J=8.2 Hz, 2H), 1.65 (d, J=3.3 Hz, 1H), 1.47, (d, J=6.2 Hz, 3H).

The alcohol 19 was converted to the title compound 20 in the same manner used for the preparation of compound of Example 16.

m.p.: 81.3°–83.6° C.

IR (KBr) cm$^{-1}$: 3462, 3194, 1656, 1600, 1569, 1471, 1448, 1263, 1224, 1148, 1039, 810, 768.

NMR (DMSO) δ: 8.90 (s, 1H), 7.25 (t, J=7.7 Hz, 1H), 7.06 (s, 1H), 6.97 (d, J=8.1 Hz, 1H), 6.94 (d, J=7.0, 1H), 6.92 (s, 1H), 6.85 (d, J=7.8 Hz, 1H), 6.49 (d, J=8.4 Hz, 1H), 6.20 (s, 2H), 5.20 (q, J=7.0 Hz, 1H), 4.22 (s, 2H), 3.75 (s, 3H), 3.26 (s, 3H), 3.26 (t, J=8.4 Hz, 2H), 2.88 (t, J=8.2 Hz, 2H), 1.36 (d, J=6.9 Hz, 3H).

EXAMPLE 18

N-Hydroxy-N-[4-{1-(3-methoxybenzyl)-indolin-5-yl}butan-2-yl]urea

A mixture of the aldehyde (18, 5.76 g, 21.6 mmol) and 1-triphenylphosphoranylidene-2-propanone (8.28 g, 26 mmol) in dry toluene (26 ml) was stirred at reflux for 4 hr. The mixture was concentrated in vacuo and purified by silica gel column (100 g) eluted with hexane-ethyl acetate (2:1) gave an yellow oil which was crystallized from hexane gave yellow solids 21(6.04 g, 91%)

NMR (CDCl$_3$) δ: 7.44 (d, J=16.1 Hz, 1H), 7.21–7.34(m, 3H), 6.79–6.91 (m, 3H), 6.51(d, J=16.1 Hz, 1H), 6.43 (d, J=8.1 Hz, 1H), 4.32 (s, 2H), 3.79 (s, 3H), 3.49 (t, J=8.6 Hz, 2H), 3.03 (t, J=8.4 Hz, 2H), 2.33 (s, 3H).

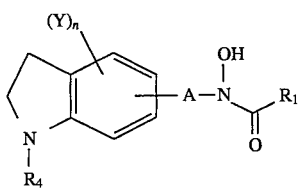

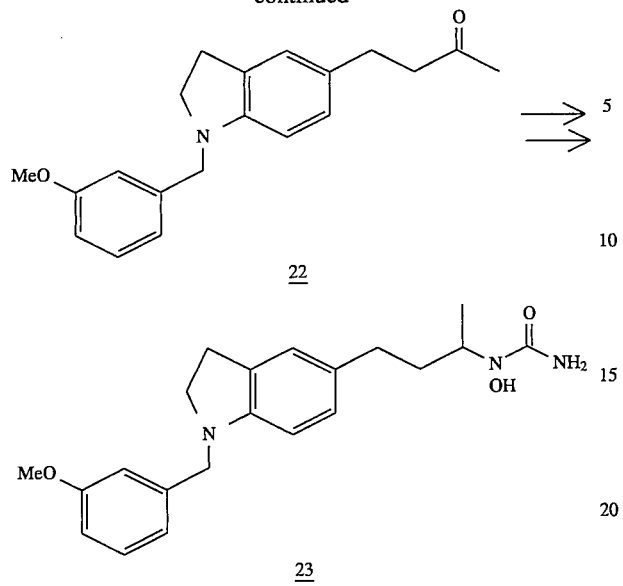

A solution of the conjugated ketone (21, 0.601 g, 1.95 mmol) in ethanol (20 ml) was hydrogenated at 25° C. and 3 atm over 5% Pd on carbon (98 mg) for 3 hr. The whole was filtered through celite and the celite cake was washed with ethanol (80 ml). The filtrate and washings were combined and concentrated in vacuo to give an yellow oil. Chromatography on silica gel eluted with hexane: ethyl acetate=4:1 to 2:1 gave a pale yellow oil (22, 480 mg, 79.6%).

NMR (CDCl$_3$) δ: 7.24 (t, J=7.9 Hz, 1H), 6.92–6.98 (m, 3H), 6.77–6.89 (m, 2H), 6.42 (d, J=8.1 Hz, 1H), 4.18 (s, 2H), 3.80 (s, 3H), 3.29 (t, J=8.2 Hz, 2H), 3.93 (t, J=8.2 Hz, 2H), 2.79 (td, J=2.6, 7.0 Hz, 2H), 2.71 (td, J=3.7, 7.0 Hz, 2H), 2.13 (s, 3H).

The ketone 22 was converted to the title compound 23 in the same manner used for the preparation of compounds of Example 1.

m.p.: 142.3°–143.2° C.

IR (KBr)cm$^{-1}$: 3474, 3356, 3170, 1652, 1458, 1440, 1274.

NMR (DMSO) δ: 8.88 (s, 1H), 7.30 (t, J=7.7 Hz, 1H), 6.94–6.98 (m, 3H), 6.88 (d, J=7.3 Hz, 1H), 6.85 (d, J=8.1 Hz, 1H), 6.51 (d, J=8.1 Hz, 1H), 6.28 (s, 2H), 4.22 (s, 2H), 4.12 (q, J=6.6 Hz, 1H), 3.78 (s, 3H), 3.25 (t, J=8.1 Hz, 2H), 2.89 (t=8.2 Hz, 2H), 1.02 (d, J=6.6 Hz, 3H).

We claim:

1. A compound of the following chemical formula or pharmaceutically acceptable salt thereof;

wherein $R_1$ is $C_1$–$C_4$ alkyl or —$NR_2R_3$;

$R_2$ and $R_3$ are each, independently, hydrogen or $C_1$–$C_4$ alkyl;

$R_4$ is $C_3$–$C_6$ cycloalkyl, $C_4$–$C_7$ cycloalkylalkyl, aryloxy $C_2$–$C_4$ alkyl, arylthio $C_2$–$C_4$ alkyl, arylamino $C_2$–$C_4$ alkyl, arylsulfinyl $C_2$–$C_4$ alkyl, aryl, aryl $C_1$–$C_6$ alkyl, aryloxyary $C_1$–$C_6$ alkyl or arylthioaryl $C_1$–$C_6$ alkyl, and the aryl groups in the said aryloxyalkyl, arylthioalkyl, arylaminoalkyl, arylsulfinylalkyl, aryl, arylalkyl, aryloxyarylalkyl and arylthioalkyl may be substituted with from 1 to 7 substituents and the substituents are each, independently, selected from the group consisting of halo, cyano, $C_1$–$C_5$ alkyl, $C_2$–$C_6$ alkenyl, $C_1$–$C_5$ alkoxy, $C_2$–$C_6$ alkenyloxy, $C_2$–$C_6$ alkoxyalkyl, halosubstituted $C_1$–$C_4$ alkyl, halosubstituted $C_1$–$C_4$ alkoxy, $C_2$–$C_5$ alkoxycarbonyl, aminocarbonyl and $C_1$–$C_4$ alkylthio;

A is $C_1$–$C_6$ alkylene, $C_3$–$C_6$ alkenylene or —O—(CH$_2$)$_m$—;

Y is each, independently, halogen, halosubstituted $C_1$–$C_6$ alkyl, $C_1$–$C_6$ alkyl, $C_2$–$C_6$ alkenyl, $C_1$–$C_6$ alkoxy or $C_3$–$C_8$ alkenyloxy;

m is 2, 3 or 4;

n is 0, 1, 2 or 3;

and provided that the substituent Y, if present, and the linking group A are attached to the aromatic ring.

2. A compound according to claim 1, wherein $R_1$ is —NH$_2$;

$R_4$ is phenyl, phenoxy $C_2$–$C_4$ alkyl, phenyl $C_1$–$C_6$ alkyl, phenoxyphenyl $C_1$–$C_6$ alkyl, mono-substituted phenyl or mono-substituted phenyl $C_1$–$C_6$ alkyl, wherein the substituent is halo, cyano, $C_1$–$C_5$ alkyl, $C_1$–$C_5$ alkoxy, CF$_3$ or OCF$_2$;

A is alkylene and n is 0.

3. A compound according to claim 2, wherein $R_4$ is phenyl, benzyl, 3-phenylpropyl, mono-substituted phenyl, mono-substituted benzyl or mono-substituted 3-phenylpropyl.

4. A compound according to claim 3 wherein $R_4$ is phenyl, benzyl or methoxybenzyl.

5. N-(1-Benzylindolin-5-yl)methyl-N-hydroxyurea.

6. N-Hydroxy-N-{1-(3-methoxybenzyl)indolin-5-yl}methylurea.

7. N-Hydroxy-N-(1-phenylindolin-5-yl)methylurea.

8. A pharmaceutical composition for the treatment of allergic or inflammatory conditions in a mammalian subject which comprises a therapeutically effective amount of a compound of claim 1 and its pharmaceutically acceptable carrier.

* * * * *